United States Patent
Errico et al.

(10) Patent No.: US 7,235,081 B2
(45) Date of Patent: *Jun. 26, 2007

(54) WEDGE PLATE INSERTER/IMPACTOR AND RELATED METHODS FOR USE IN IMPLANTING AN ARTIFICIAL INTERVERTEBRAL DISC

(75) Inventors: Joseph P. Errico, Green Brook, NJ (US); Michael W. Dudasik, Nutley, NJ (US); Rafail Zubok, Midland Park, NJ (US)

(73) Assignee: SpineCore, Inc., Summit, NJ (US)

( * ) Notice: Subject to any disclaimer, the term of this patent is extended or adjusted under 35 U.S.C. 154(b) by 34 days.

This patent is subject to a terminal disclaimer.

(21) Appl. No.: 10/425,267

(22) Filed: Apr. 29, 2003

(65) Prior Publication Data

US 2003/0229358 A1    Dec. 11, 2003

Related U.S. Application Data

(63) Continuation-in-part of application No. 10/282,356, filed on Oct. 29, 2002, now Pat. No. 7,169,182, which is a continuation-in-part of application No. 10/256,160, filed on Sep. 26, 2002, now Pat. No. 6,989,032, which is a continuation-in-part of application No. 10/175,417, filed on Jun. 19, 2002, which is a continuation-in-part of application No. 10/151,280, filed on May 20, 2002, which is a continuation-in-part of application No. 09/970,479, filed on Oct. 4, 2001, now Pat. No. 6,669,730, and a continuation-in-part of application No. 10/140,153, filed on May 7, 2002, said application No. 09/970,479 is a continuation-in-part of application No. 09/968,046, filed on Oct. 1, 2001, said application No. 10/140,153 is a continuation-in-part of application No. 09/970,479, and a continuation-in-part of application No. 10/128,619, filed on Apr. 23, 2002, which is a continuation-in-part of application No. 09/906,119, filed on Jul. 16, 2001, and a continuation-in-part of application No. 09/982,148, filed on Oct. 18, 2001.

(51) Int. Cl.
*A61B 17/56* (2006.01)
(52) U.S. Cl. .................. 606/99; 606/61; 623/17.15
(58) Field of Classification Search .................. 606/99, 606/61, 1, 204, 217, 206, 79–81, 91, 100; 623/17.15
See application file for complete search history.

(56) References Cited

U.S. PATENT DOCUMENTS 2,193,122 A    3/1940    Crabbs (Continued)

FOREIGN PATENT DOCUMENTS

DE    19903763 A1 *   8/2000

(Continued)

*Primary Examiner*—Brian E. Pellegrino
(74) *Attorney, Agent, or Firm*—Lerner, David, Littenberg, Krumholz & Mentlik, LLP

(57) ABSTRACT

A wedge plate inserter/impactor instrument is provided primarily for holding, inserting, repositioning, removing, impacting, extracting, and otherwise manipulating an artificial intervertebral disc having features suitable for being manipulated thereby. A spring-loaded holding pin of the instrument can be used to engage a corresponding hole on the disc and confront the angled surfaces of the disc to enable the holding and manipulation of the disc. A forward wedge extension of the inserter/impactor has upper and lower surfaces that engage inwardly facing surfaces of the disc to hold the baseplates of the disc at a preferred lordosis angle with respect to one another. The instrument can engage the disc from a variety of surgical approach angles.

8 Claims, 5 Drawing Sheets

U.S. PATENT DOCUMENTS

| | | |
|---|---|---|
| 3,867,728 A | 2/1975 | Stubstad et al. |
| 4,309,777 A | 1/1982 | Patil |
| 4,566,466 A | 1/1986 | Ripple et al. |
| 4,605,417 A | 8/1986 | Fleischauer |
| 4,759,766 A | 7/1988 | Buettner-Janz et al. |
| 4,759,769 A | 7/1988 | Hedman et al. |
| 4,932,969 A | 6/1990 | Frey et al. |
| 4,997,432 A | 3/1991 | Keller |
| 5,034,254 A | 7/1991 | Cologna et al. |
| 5,112,178 A | 5/1992 | Overhues et al. |
| 5,122,130 A | 6/1992 | Keller |
| 5,236,460 A | 8/1993 | Barber |
| 5,258,031 A | 11/1993 | Salib et al. |
| 5,306,308 A | 4/1994 | Gross et al. |
| 5,314,477 A | 5/1994 | Marnay |
| 5,370,697 A | 12/1994 | Baumgartner |
| 5,401,269 A | 3/1995 | Buttner-Janz et al. |
| 5,425,773 A | 6/1995 | Boyd et al. |
| 5,458,642 A | 10/1995 | Beer et al. |
| 5,507,816 A | 4/1996 | Bullivant |
| 5,556,431 A | 9/1996 | Buttner-Janz |
| 5,562,738 A | 10/1996 | Boyd et al. |
| 5,674,296 A | 10/1997 | Bryan et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,720,751 A | 2/1998 | Jackson |
| 5,755,796 A | 5/1998 | Ibo et al. |
| 5,782,830 A | 7/1998 | Farris |
| 5,782,832 A | 7/1998 | Larsen et al. |
| 5,827,328 A | 10/1998 | Buttermann |
| 5,860,990 A * | 1/1999 | Nobles et al. .............. 606/144 |
| 5,865,846 A | 2/1999 | Bryan et al. |
| 5,888,226 A | 3/1999 | Rogozinski |
| 5,893,889 A | 4/1999 | Harrington |
| 5,895,428 A | 4/1999 | Berry |
| 5,899,941 A | 5/1999 | Nishijima et al. |
| 5,926,685 A | 7/1999 | Krebs et al. |
| 5,989,291 A | 11/1999 | Ralph et al. |
| 5,989,294 A | 11/1999 | Marlow |
| 6,001,130 A | 12/1999 | Bryan et al. |
| 6,019,792 A | 2/2000 | Cauthen |
| 6,039,763 A | 3/2000 | Shelokov |
| 6,050,999 A * | 4/2000 | Paraschac et al. .............. 606/1 |
| 6,063,121 A | 5/2000 | Xavier et al. |
| 6,066,174 A | 5/2000 | Farris |
| 6,113,637 A | 9/2000 | Gill et al. |
| 6,113,639 A | 9/2000 | Ray et al. |
| 6,136,031 A | 10/2000 | Middleton |
| 6,146,421 A | 11/2000 | Gordon et al. |
| 6,156,067 A | 12/2000 | Bryan et al. |
| 6,159,215 A | 12/2000 | Urbahns et al. |
| 6,174,311 B1 | 1/2001 | Branch et al. |
| 6,179,874 B1 | 1/2001 | Cauthen |
| 6,224,607 B1 | 5/2001 | Michelson |
| 6,228,023 B1 * | 5/2001 | Zaslavsky et al. .............. 606/1 |
| 6,228,118 B1 | 5/2001 | Gordon |
| 6,241,732 B1 | 6/2001 | Overaker et al. |
| 6,280,458 B1 | 8/2001 | Boche et al. |
| 6,319,257 B1 | 11/2001 | Carignan et al. |
| 6,368,350 B1 | 4/2002 | Erickson et al. |
| 6,375,682 B1 | 4/2002 | Fleischmann et al. |
| 6,416,551 B1 | 7/2002 | Keller |
| 6,428,544 B1 | 8/2002 | Ralph et al. |
| 6,436,102 B1 | 8/2002 | Ralph et al. |
| 6,471,725 B1 | 10/2002 | Ralph et al. |
| 6,478,796 B2 | 11/2002 | Zucherman et al. |
| 6,478,800 B1 | 11/2002 | Fraser et al. |
| 6,478,801 B1 | 11/2002 | Ralph et al. |
| 6,517,580 B1 | 2/2003 | Ramadan et al. |
| 6,527,786 B1 * | 3/2003 | Davis et al. ................. 606/151 |
| 6,527,804 B1 | 3/2003 | Gauchet et al. |
| 6,554,864 B2 | 4/2003 | Ralph et al. |
| 6,562,047 B2 | 5/2003 | Ralph et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,592,624 B1 | 7/2003 | Fraser et al. |
| 6,607,559 B2 | 8/2003 | Ralph et al. |
| 6,610,092 B2 | 8/2003 | Ralph et al. |
| 6,610,093 B1 | 8/2003 | Pisharodi |
| 6,623,525 B2 | 9/2003 | Ralph et al. |
| 6,645,249 B2 | 11/2003 | Ralph et al. |
| 6,652,233 B2 | 11/2003 | Otake |
| 6,652,533 B2 | 11/2003 | O'Neil |
| 6,669,699 B2 | 12/2003 | Ralph et al. |
| 6,669,732 B2 | 12/2003 | Serhan et al. |
| 6,673,113 B2 | 1/2004 | Ralph et al. |
| 6,682,562 B2 | 1/2004 | Viart et al. |
| 6,692,495 B1 | 2/2004 | Zacouto |
| 6,706,068 B2 | 3/2004 | Ferree |
| 6,716,245 B2 | 4/2004 | Pasquet et al. |
| 6,827,743 B2 | 12/2004 | Eisermann et al. |
| 6,863,689 B2 | 3/2005 | Ralph et al. |
| 2001/0007073 A1 | 7/2001 | Zucherman et al. |
| 2001/0012938 A1 | 8/2001 | Zuckerman et al. |
| 2001/0016773 A1 | 8/2001 | Serhan et al. |
| 2001/0020170 A1 | 9/2001 | Zucherman et al. |
| 2001/0039452 A1 | 11/2001 | Zucherman et al. |
| 2002/0045904 A1 * | 4/2002 | Fuss et al. .................... 606/99 |
| 2002/0062131 A1 | 5/2002 | Gallo, Sr. |
| 2002/0082695 A1 | 6/2002 | Neumann |
| 2002/0099377 A1 | 7/2002 | Zucherman et al. |
| 2002/0111679 A1 | 8/2002 | Zucherman et al. |
| 2002/0111681 A1 | 8/2002 | Ralph et al. |
| 2002/0111682 A1 | 8/2002 | Ralph et al. |
| 2002/0111684 A1 | 8/2002 | Ralph et al. |
| 2002/0111685 A1 | 8/2002 | Ralph et al. |
| 2002/0128714 A1 | 9/2002 | Manasas et al. |
| 2002/0161375 A1 | 10/2002 | Ralph et al. |
| 2003/0014057 A1 | 1/2003 | Ralph et al. |
| 2003/0014109 A1 | 1/2003 | Ralph et al. |
| 2003/0014110 A1 | 1/2003 | Ralph et al. |
| 2003/0014112 A1 | 1/2003 | Ralph et al. |
| 2003/0014113 A1 | 1/2003 | Ralph et al. |
| 2003/0014114 A1 | 1/2003 | Ralph et al. |
| 2003/0014115 A1 | 1/2003 | Ralph et al. |
| 2003/0014116 A1 | 1/2003 | Ralph et al. |
| 2003/0023245 A1 | 1/2003 | Ralph et al. |
| 2003/0023309 A1 | 1/2003 | Ralph et al. |
| 2003/0023310 A1 | 1/2003 | Ralph et al. |
| 2003/0028197 A1 | 2/2003 | Hanson et al. |
| 2003/0028249 A1 | 2/2003 | Baccelli et al. |
| 2003/0028252 A1 | 2/2003 | Ralph et al. |
| 2003/0040801 A1 | 2/2003 | Ralph et al. |
| 2003/0055503 A1 | 3/2003 | O'Neil |
| 2003/0060886 A1 | 3/2003 | Van Hoeck et al. |
| 2003/0065395 A1 | 4/2003 | Ralph et al. |
| 2003/0069586 A1 | 4/2003 | Errico et al. |
| 2003/0069642 A1 | 4/2003 | Ralph et al. |
| 2003/0074067 A1 | 4/2003 | Errico et al. |
| 2003/0078666 A1 | 4/2003 | Ralph et al. |
| 2003/0083747 A1 | 5/2003 | Winterbottom et al. |
| 2003/0100951 A1 | 5/2003 | Serhan et al. |
| 2003/0109928 A1 | 6/2003 | Pasquet et al. |
| 2003/0125748 A1 | 7/2003 | Li et al. |
| 2003/0135278 A1 | 7/2003 | Eckman |
| 2003/0149438 A1 | 8/2003 | Nichols et al. |
| 2003/0149482 A1 | 8/2003 | Michelson |
| 2003/0187508 A1 | 10/2003 | Cauthen |
| 2003/0191534 A1 | 10/2003 | Viart et al. |
| 2003/0199981 A1 | 10/2003 | Ferree |
| 2003/0204260 A1 | 10/2003 | Ferree |

| | | |
|---|---|---|
| 2003/0208271 A1 | 11/2003 | Kuras |
| 2003/0216744 A1 | 11/2003 | Longhini et al. |
| 2003/0216810 A1 | 11/2003 | Ralph et al. |
| 2003/0225408 A1 | 12/2003 | Nichols et al. |
| 2003/0225416 A1 | 12/2003 | Bonvallet et al. |
| 2003/0229358 A1 | 12/2003 | Errico et al. |
| 2003/0233097 A1 | 12/2003 | Ferree |
| 2003/0233148 A1 | 12/2003 | Ferree |
| 2004/0002759 A1 | 1/2004 | Ferree |
| 2004/0002762 A1 | 1/2004 | Hawkins |
| 2004/0010316 A1 | 1/2004 | William et al. |
| 2004/0024406 A1 | 2/2004 | Ralph et al. |
| 2004/0024407 A1 | 2/2004 | Ralph et al. |
| 2004/0030387 A1 | 2/2004 | Landry et al. |
| 2004/0030389 A1 | 2/2004 | Ferree |
| 2004/0030390 A1 | 2/2004 | Ferree |
| 2004/0034426 A1 | 2/2004 | Errico et al. |
| 2004/0078079 A1 | 4/2004 | Foley |

FOREIGN PATENT DOCUMENTS

| | | |
|---|---|---|
| EP | 0 392 076 A1 | 10/1990 |
| FR | 2 718 635 A1 | 4/1994 |
| WO | WO-94/04100 | 3/1994 |
| WO | WO-97/10776 A2 | 3/1997 |
| WO | WO-03/084449 A1 | 10/2003 |

* cited by examiner

C-C (FROM FIG. 1C)

A-A (FROM FIG. 1A)

B-B (FROM FIG. 1A)

WEDGE PLATE INSERTER/IMPACTOR AND RELATED METHODS FOR USE IN IMPLANTING AN ARTIFICIAL INTERVERTEBRAL DISC

CROSS-REFERENCE TO RELATED APPLICATIONS

The present application is a continuation-in-part application of U.S. patent application Ser. No. 10/282,356 (filed Oct. 29, 2002 now U.S. Pat. No. 7,169,182) entitled "Instrumentation and Methods For Use In Implanting an Artificial Intervertebral Disc", which is a continuation-in-part application of U S. patent application Ser. No. 10/256,160 (filed Sep. 26, 2002 now U.S. Pat. No. 6,989,032) entitled "Artificial Intervertebral Disc Having Limited Rotation Using a Captured Ball and Socket Joint With a Solid Ball and Compression Locking Post", which is a continuation-in-part application of U.S. patent application Ser. No. 10/175,417 (filed Jun. 19, 2002) entitled "Artificial Intervertebral Disc Utilizing a Ball Joint Coupling", which is a continuation-in-part application of U S. patent application Ser. No. 10/151,280 (filed May 20, 2002) entitled "Tension Bearing Artificial Disc Providing a Centroid of Motion Centrally Located Within an Intervertebral Space", which is a continuation-in-part application of both U.S. patent application Ser. No. 09/970,479 (filed Oct. 4, 2001 now U.S. Pat. No. 6,669,730) entitled "Intervertebral Spacer Device Utilizing a Spirally Slotted Belleville Washer Having Radially Extending Grooves" as well as U.S. patent application Ser. No. 10/140,153 (filed May 7, 2002) entitled "Artificial Intervertebral Disc Having a Flexible Wire Mesh Vertebral Body Contact Element", the former being a continuation-in-part application of U.S. patent application Ser. No. 09/968,046 (filed Oct. 1, 2001) entitled "Intervertebral Spacer Device Utilizing a Belleville Washer Having Radially Extending Grooves" and the latter being a continuation-in-part application of both U.S. patent application Ser. No. 09/970,479 (detailed above) as well as U.S. patent application Ser. No. 10/128,619 (filed Apr. 23, 2002) entitled "Intervertebral Spacer Having a Flexible Wire Mesh Vertebral Body Contact Element", which is a continuation-in-part application of both U.S. patent application Ser. No. 09/906,119 (filed Jul. 16, 2001) and entitled "Trial Intervertebral Distraction Spacers" as well as U.S. patent application Ser. No. 09/982,148 (filed Oct. 18, 2001) and entitled "Intervertebral Spacer Device Having Arch Shaped Spring Elements". All of the above mentioned applications are hereby incorporated by reference herein in their respective entireties.

FIELD OF THE INVENTION

This invention relates generally to systems and methods for use in spine arthroplasty, and more specifically to instruments for inserting and impacting artificial intervertebral discs, and methods of use thereof.

BACKGROUND OF THE INVENTION

The bones and connective tissue of an adult human spinal column consists of more than twenty discrete bones coupled sequentially to one another by a tri-joint complex that consists of an anterior disc and the two posterior facet joints, the anterior discs of adjacent bones being cushioned by cartilage spacers referred to as intervertebral discs. These more than twenty bones are anatomically categorized as being members of one of four classifications: cervical, thoracic, lumbar, or sacral. The cervical portion of the spine, which comprises the top of the spine, up to the base of the skull, includes the first seven vertebrae. The intermediate twelve bones are the thoracic vertebrae, and connect to the lower spine comprising the five lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. With respect to the failure of the intervertebral disc, and the insertion of implants and/or height restorative devices, several methods and devices have been disclosed in the prior art that achieve immobilization and/or fusion of adjacent bones by implanting artificial assemblies in or on the spinal column. More recently, the development of non-fusion implant devices, which purport to permit continued natural movement in the tri-joint complex, have provided great promise as a preferably alternative to fusion devices. The region of the back that needs to be corrected, as well as the individual variations in anatomy, determine the appropriate surgical protocol and implantation assembly. Generally, the preparation of the intervertebral space for the receipt of fusion or non-fusion devices involves removing the damaged disc material and thereafter distracting the adjacent vertebral bones to their appropriate distance apart. Once the proper height of the intervertebral space is restored, the fusion or non-fusion device can be implanted.

It is an object of the invention to provide instrumentation and methods that enable surgeons to more accurately, easily, and efficiently implant fusion or non-fusion devices. Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which includes, among other aspects, an inserter/impactor (sometimes referred to herein as an "inserter/impactor") useful for holding and manipulating artificial intervertebral discs.

More particularly, the systems and methods disclosed herein are intended for use in spine arthroplasty procedures, and specifically for use with the systems and methods described herein in conjunction with the systems and methods in conjunction with the systems and methods described in U.S. patent application Ser. No. 10/282,356 (filed Oct. 29, 2002) entitled "Instrumentation and Methods For Use In Implanting an Artificial Intervertebral Disc" (hereinafter referred to as "the '356 application") as well as U.S. patent application Ser. No. 10/256,160 (filed Sep. 26, 2002)

entitled "Artificial Intervertebral Disc Having Limited Rotation Using a Captured Ball and Socket Joint With a Solid Ball and Compression Locking Post" (hereinafter referred to as "the '160 application") as well as U.S. patent application Ser. No. 09/906,127 (filed Jul. 16, 2001) entitled "Insertion Tool For Use With Intervertebral Spacers" (hereinafter referred to as "the '127 application"), both applications of which are mentioned above. However, it should be understood that the systems and methods described herein are also suitable for use with other systems and methods without departing from the scope of the invention.

While the instrumentation described herein (e.g., the inserter/impactor) will be discussed for use with the artificial intervertebral disc of FIG. 1 of the present application (hereinafter, such figures will merely be referred to as "FIG. 1"), such discussions are merely by way of example and not intended to be limiting of their uses. Thus, it should be understood that the instrumentation and methods can be used with any of the artificial intervertebral discs disclosed in the '356 or '160 applications, or any other artificial intervertebral disc having (or being modifiable or modified to have) suitable features therefor. Moreover, it is anticipated that the features of the artificial intervertebral discs (e.g., plate surfaces and engagement holes) that are used by the inserter/impactor discussed herein to hold and/or manipulate the artificial intervertebral disc can be applied, individually, or collectively or in various combinations, to other trials, spacers, artificial intervertebral discs, or other orthopedic devices as stand-alone innovative features for enabling such trials, spacers, artificial intervertebral discs, or other orthopedic devices to be more efficiently and more effectively held and/or manipulated by the inserter/impactor described herein or by tools having suitable features. In addition, it should be understood that the invention encompasses instrumentation and methods for implanting artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

Preferably, with regards to each artificial intervertebral disc to be implanted, a plurality of sizes of the artificial intervertebral disc would be available (e.g., the artificial intervertebral disc 160 of FIG. 1). That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. It should be understood that the artificial intervertebral discs can be offered in a variety of dimensions without departing from the scope of the invention, and that the dimensions specifically identified and quantified herein are merely exemplary. Each of the plurality of artificial intevertebral disc preferably further includes features that can be used by the inserter/impactor (described below) and/or the inserter/impactor described in the '356 application.

With regard to features that can be used by the inserter/impactor described in the '356 application, each artificial intervertebral disc includes an anteriorly facing flat surface, flanked by two anteriolaterally facing flat surfaces (one on each side of the anteriorly facing flat surface), and, to provide for holding of the disc for an anterior insertion approach, a hole spaced from the anteriorly facing flat surface, the hole having a longitudinal axis parallel to the anteriorly facing flat surface. The holding pin of the inserter/impactor fits within the hole, and the angled flat surfaces of the disc fit against the correspondingly angled flat surfaces of the inserter/impactor, and operation of the inserter/impactor pulls the holding pin toward the flat surface of the inserter/impactor opposite the pin, to rigidly hold the disc by the lower baseplate. The holding pin protrudes from the wedge-shaped extended surface of the distal end of the inserter/impactor and is restricted from upward movement with respect to the distal head by the presence of the wedge-shaped extended surface of the distal end of the inserter/impactor. More particularly, with any attempted upward movement of the holding pin, the pin encounters the upper surface of the channel in which the pin travels, preventing any such upward movement. When the intervertebral disc is held in this manner, rotation of the disc about a longitudinal axis relative to the inserter/impactor is prevented by interference of the corners of the disc's flat surfaces and the corners of the inserter/impactor's flat surfaces, similar to the manner in which a wrench holding a nut prevents rotation of the nut relative to the wrench. Further, when the disc is held in this manner, rotation of the disc about a lateral axis of the disc relative to the inserter/impactor is prevented by interference of the inwardly facing surface of the first baseplate (e.g., upper baseplate) of the disc and the corresponding surface (e.g., upper surface) of the wedge on the distal end, and by interference of the inwardly facing surface of the second baseplate (e.g., lower baseplate) of the disc and the corresponding surface (e.g., lower surface) of the wedge on the distal end. It is preferable that the wedge on the inserter/impactor will interfere between the first and second baseplates (e.g., upper and lower) so that the surfaces of the first and second baseplates align at a preferred 15 degrees angle of lordosis when the disc is held by the inserter/impactor.

Preferably, in order to provide for a holding of the disc for two additional (here, anteriolateral) insertion approaches, each disc also include two additional holes, one spaced apart from one of the anteriolaterally facing flat surfaces, and the other spaced apart from the other of the anteriolaterally facing flat surfaces. Accordingly, operation of the inserter/impactor can fit the holding pin into either of these two additional holes, and hold the anteriolaterally facing flat surface (the one associated with the hole into which the pin is fit) of the disc against the flat surface of the inserter/impactor opposite the pin. It should be understood that preferably, in order to facilitate these two additional approaches, the angle separating the anteriorly facing flat surface of the disc and one of the anteriolaterally facing flat surfaces of the disc is equal to the angle separating the anteriorly facing flat surface and the other of the anteriolaterally facing flat surfaces.

DETAILED DESCRIPTION OF THE PREFERRED EMBODIMENTS

Figure 1A:
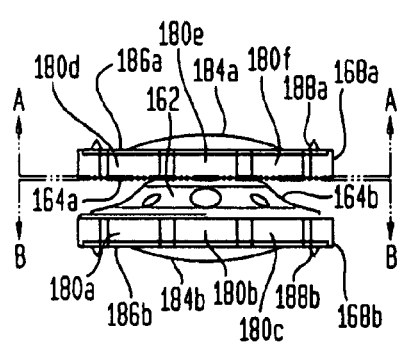
FIG. 1 of the present application show front (FIG. 1a), side cutaway (FIG. 1b), top (FIG. 1c), perspective cutaway (FIG. 1d), bottom cutaway (FIG. 1e), top cutaway (FIG. 1f), bottom perspective (FIG. 1g), and top perspective (FIG. 1h) views of an exemplary artificial intervertebral disc for use with the present invention.
Figure 1B:
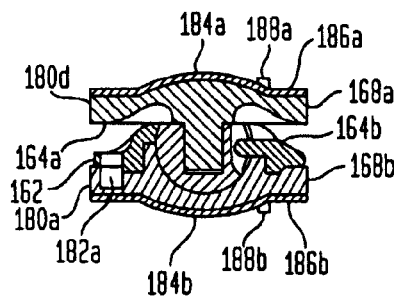
Figure 1C:
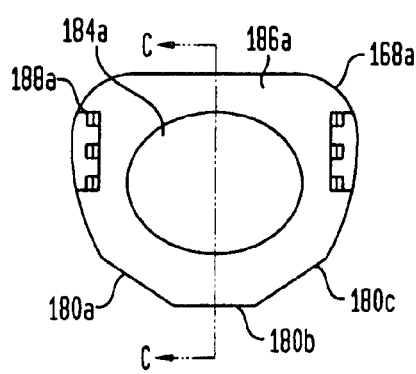
Figure 1D:
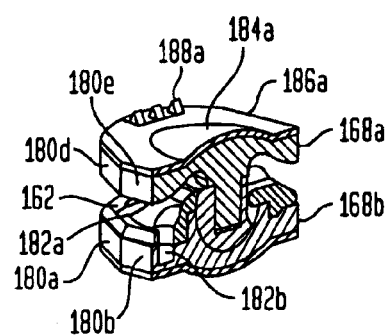
Figure 1E:
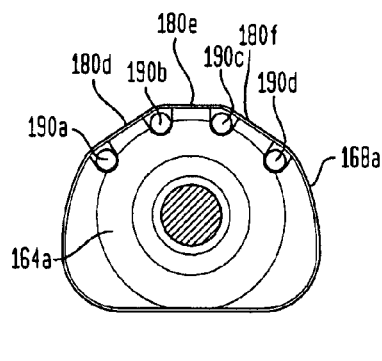
Figure 1F:
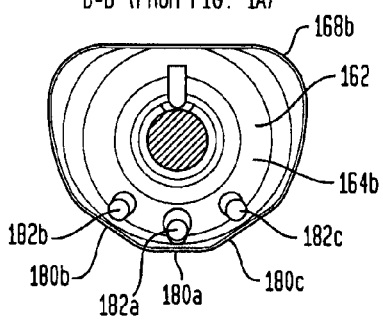
Figure 1G:
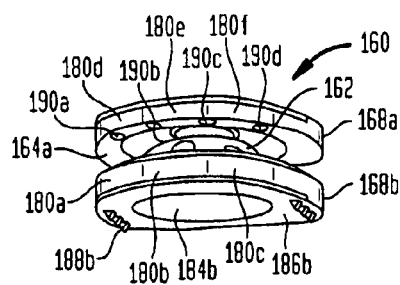
Figure 1H:
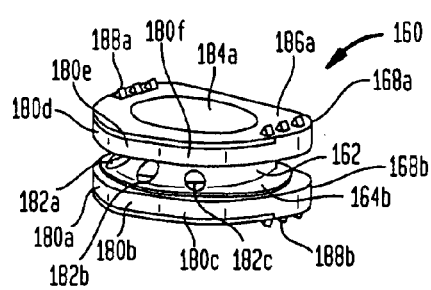
Figure 2A:
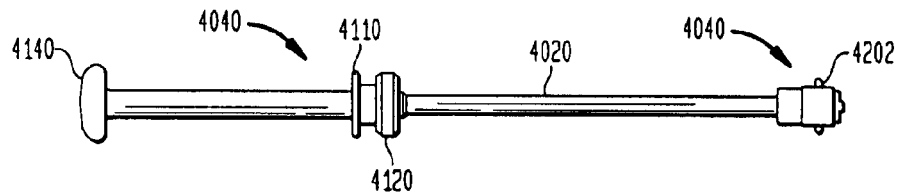
FIGS. 2a–c show side (FIG. 2a), perspective (FIG. 2b), and close-up perspective (FIG. 2c) views of a wedge plate inserter/impactor of the present invention.
Figure 2B:
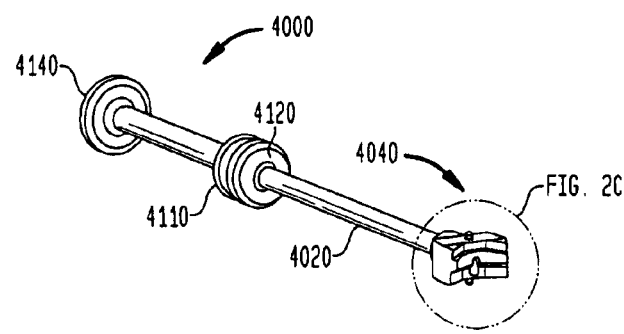
Figure 2C:
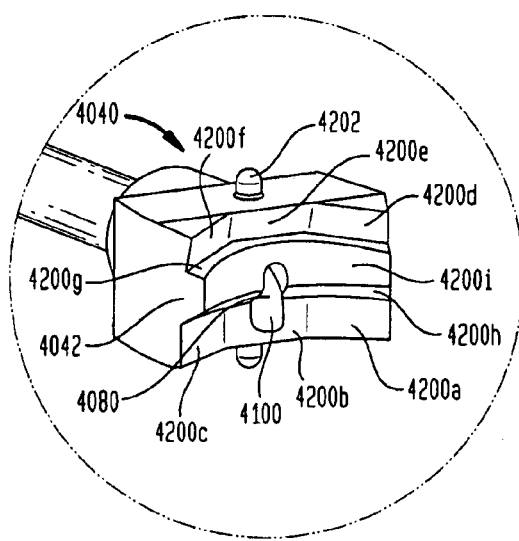
Figure 3A:
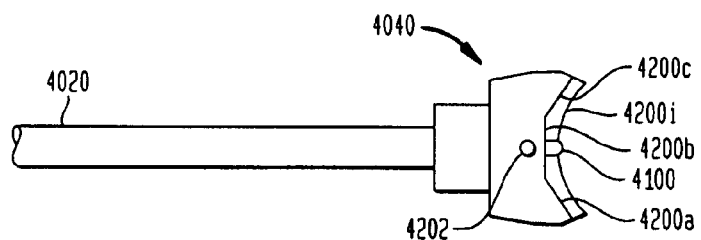
FIGS. 3a–d show bottom (FIG. 3a), side (FIG. 3b), top (FIG. 3c), and side cutaway (FIG. 3d) views of a distal end of a wedge plate inserter/impactor of the present invention.
Figure 3B:
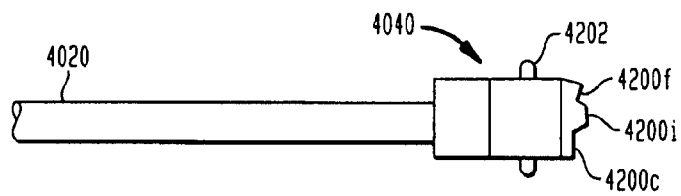
Figure 3C:
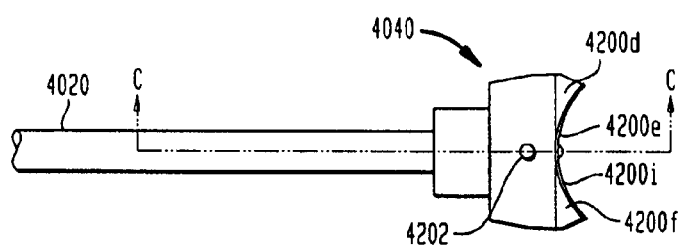
Figure 3D:
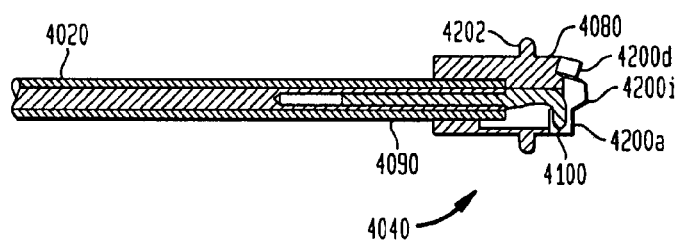

While the invention will be described more fully hereinafter with reference to the accompanying drawings, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

A preferred embodiment of an artificial intervertebral disc (e.g., artificial intervertebral disc 160) for use with the instrumentation of the present invention is referenced and described in the '356 application, and the same description is hereby incorporated by reference herein. The artificial intervertebral disc illustrated in FIGS. 1a–h of the present application is discussed herein with reference to such figures, as an example of an artificial intervertebral disc suitable for use with the present invention.

Referring now to FIGS. 1a–h, an artificial intervertabral disc of the present invention is shown in front (FIG. 1a), side cutaway (FIG. 1b), top (FIG. 1c), side cutaway (FIG. 1d), bottom cutaway (FIG. 1e), top cutaway (FIG. 1f), bottom perspective (FIG. 1g), and top perspective (FIG. 1h) views.

It should be understood that the illustration and reference herein to the artificial intervertebral disc shown in FIGS. 1a–1h is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being manipulated by the instrumentation and methods described herein are contemplated by the present invention. Indeed, the features suitable for manipulation (e.g., angled flat surfaces with adjacent holes) are encompassed by the present invention, regardless of to what orthopedic device they may be applied. Other exemplary suitable artificial intervertebral discs include, but are not limited to, the artificial intervertebral discs described in the '160 application. The artificial intervertebral disc shown in FIGS. 1a–1h has features similar to those of these other suitable artificial intervertebral discs of the '160 application, and it should be understood that such similar features are structurally and functionally as described in the '160 application. Such similar features include an inwardly facing surface of the upper baseplate 164a, and a convex structure 162 on the lower baseplate 168b, the convex structure 162 having an inwardly facing surface 164b.

And, while the instrumentation described herein will be discussed for use with the artificial intervertebral disc of FIGS. 1a–1h, such discussions are merely by way of example and are not intended to be limiting of their uses. Thus, it should be understood that the tools can be used with any of the artificial intervertebral discs disclosed in the '160 application, or any other artificial intervertebral disc having (or being modifiable or modified to have) suitable features therefor. Moreover, it is anticipated that the features of the artificial intervertebral disc (e.g., the flat surfaces and accompanying holes) and/or the static trials (e.g., the cylindrical trunks and flat surfaces and accompanying holes) that are used by the tools discussed herein to hold and/or manipulate these devices can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein or by other tools having similar features. In addition, it should be understood that the invention encompasses artificial intervertebral discs, spacers, trials (static or dynamic), and/or other orthopedic devices, that have one or more of the features disclosed herein, in any combination, and that the invention is therefore not limited to artificial intervertebral discs, spacers, trials, and/or other orthopedic devices having all of the features simultaneously.

A plurality of static trials are provided primarily for use in determining the appropriate size of an artificial intervertebral disc to be implanted (or whether a particular size of the artificial intervertebral disc can be implanted) into the distracted intervertebral space (e.g., the artificial intervertebral disc 160 of FIGS. 1a–1h). Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs. Accordingly, preferably, each of the plurality of static trials for use with a particular plurality of differently sized artificial intervertebral discs would have a respective width and depth dimension set corresponding to the width and depth of a respective one of the plurality of differently sized artificial intervertebral discs. For example, the plurality of static trials for use with the set of artificial intervertebral discs described for example could include static trials having widths being either 35 mm or 40 mm, and depths ranging from 14 mm to 18 mm in 1 mm increments, for a total of 10 static trials. It should be understood that the artificial intervertebral discs and/or the static trials can be offered in a variety of dimensions without departing from the scope of the invention, and that the dimensions specifically identified and quantified herein are merely exemplary. Moreover, it should be understood that the set of static trials need not include the same number of trials for each artificial intervertebral disc in the set of artificial intervertebral discs, but rather, none, one, or more than one trial can be included in the trial set for any particular artificial intervertebral disc in the set.

A preferred embodiment of a wedge plate inserter/impactor of the present invention will now be described.

Figure 4A:
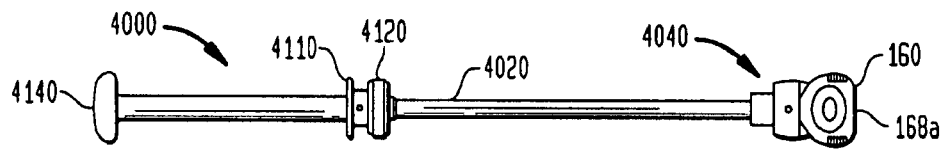
FIGS. 4a–b show top (FIG. 4a) and side (FIG. 4b) views of a wedge plate inserter/impactor of the present invention holding an exemplary artificial intervertebral disc.
Figure 4B:
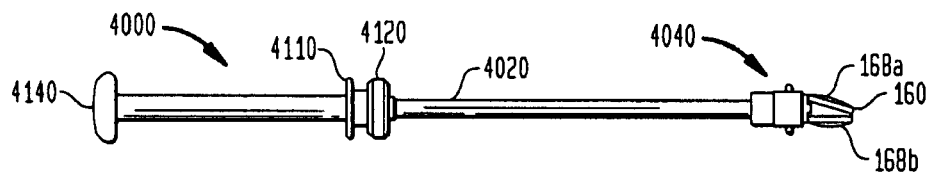
Figure 4C:
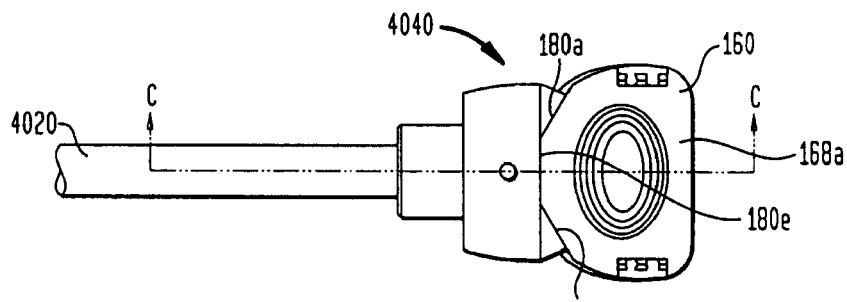
FIGS. 4c–e show top (FIG. 4c), side (FIG. 4d), and side cutaway (FIG. 4e) views of a distal end of a wedge plate inserter/impactor of the present invention holding an exemplary artificial intervertebral disc.
Figure 4D:
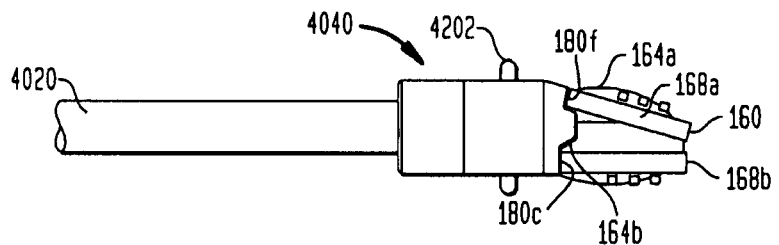
Figure 4E:
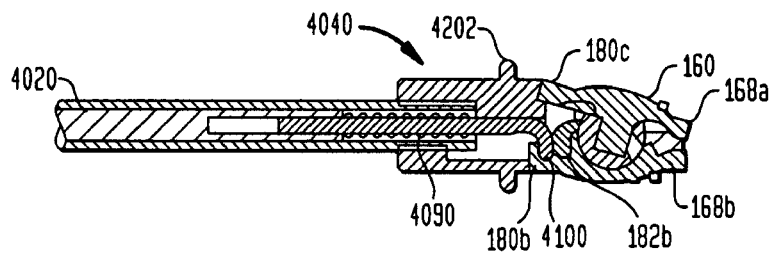

Referring now to FIGS. 2a–4e, FIGS. 2a–c side (FIG. 2a), perspective (FIG. 2b), and close-up perspective (FIG. 2c), and perspective (FIG. 4d) views of a wedge plate inserter/ impactor of the present invention. FIGS. 3a–d show bottom (FIG. 3a), side (FIG. 3b), top (FIG. 3c), and side cutaway (FIG. 3d) views of a distal end of a wedge plate inserter/impactor of the present invention. FIGS. 4a–b show top (FIG. 4a) and side (FIG. 4b) views of a wedge plate inserter/impactor of the present invention holding an exemplary artificial intervertebral disc. FIGS. 4c–e show top (FIG. 4c), side (FIG. 4d), and side cutaway (FIG. 4e) views of a distal end of a wedge plate inserter/impactor of the present invention holding an exemplary artificial intervertebral disc.

It should be understood that the illustration and reference herein to the artificial intervertebral disc shown in FIGS. 1a–h of the present application is merely to show an example of one type of artificial intervertebral disc that is contemplated by, encompassed by, and suitable for use with, the present invention, and that such illustration and reference herein is not meant to limit the scope of the present invention or limit the uses of the present invention. Rather, any other artificial intervertebral disc (or any other orthopedic device) having suitable features for being used with the instrumentation and methods described herein are contemplated by the present invention. Indeed, the features suitable for manipulation (e.g., angled flat surfaces with adjacent holes and/or opposing notches, and/or inwardly facing baseplate surfaces) are encompassed by the present invention, regardless of to what orthopedic device they may be applied. Other exemplary suitable artificial intervertebral discs include, but are not limited to, the artificial intervertebral discs described in the '160 application with regard to FIGS. 8a–y, 9a–t, 10a–t, 11a–j, and 12a–o thereof and by the accompanying descriptions therefor (e.g., embodiments identified as the first, second, third, fourth, and fifth preferred embodiments of the fourth embodiment family, etc.). It should be noted that, as can be seen from FIG. 1a–h of the present application, that the artificial intervertebral disc shown in FIG. 11–h of the present application has features similar to those of these other suitable artificial intervertebral discs of the '160 application, and it should be understood that such similar features are structurally and functionally as described in the '160 application. Such similar features include an inwardly facing surface of the upper baseplate, and a convex structure on the lower baseplate, the convex structure having an inwardly facing surface.

And, while the instrumentation described herein (e.g., the inserter/impactor) as well as the instrumentation described in the '356 application (e.g., the inserter/impactor described therein) will be discussed for use with the artificial intervertebral disc of FIGS. 1a–h of the present application, such discussions are merely by way of example and not intended to be limiting of their uses. Thus, it should be understood that the tools can be used with any of the artificial intervertebral discs disclosed in the '356 application or the '160 application, or any other artificial intervertebral disc having (or being modifiable or modified to have) suitable features therefor. Moreover, it is anticipated that the features of the artificial intervertebral disc (e.g., the angled flat surfaces and the inwardly facing baseplate surfaces, and accompanying holes) that are used by the tool discussed herein (or in the '356 application) to hold and/or manipulate these devices (certain features, it should be noted, were first shown and disclosed in the '160 application, the '127 application, and/or the '356 application) can be applied, individually or collectively or in various combinations, to other trials, spacers, artificial intervertebral discs or other orthopedic devices as stand-alone innovative features for enabling such trials, spacers, artificial intervertebral discs, or other orthopedic devices to be more efficiently and more effectively held and/or manipulated by the tools described herein (or in the '356 application) or by other tools having suitable features. In addition, it should be understood that the invention encompasses artificial intervertebral discs, spacers, trials (static or dynamic), and/or other orthopedic devices, that have one or more of the features disclosed herein (or in the '356 application), in any combination, and that the invention is therefore not limited to artificial intervertebral discs, spacers, trials, and/or other orthopedic devices having all of the features simultaneously.

Preferably, for each artificial intervertebral disc to be implanted, a plurality of sizes of the artificial intervertebral disc would be available. That is, preferably, a plurality of the same type of artificial intervertebral disc would be available, each of the plurality having a respective width and depth dimension combination that allows it to fit within a correspondingly dimensioned intervertebral space. For example, the plurality of artificial intervertebral discs could include artificial intervertebral discs having widths being either 35 mm or 40 mm, and depths ranging from 14 mm to 18 mm in 1 mm increments, for a total of 10 discs.

The inserter/impactor 4000 is provided primarily for holding, inserting, repositioning, removing, impacting, extracting, and otherwise manipulating an artificial intervertebral disc having features suitable for being manipulated by the inserter/impactor. (However, it can also be used to hold, insert, reposition, remove, impact, extract, and otherwise manipulate any other orthopedic device having suitable features therefor. For example, it should be understood that distraction of an intervertebral space can be accomplished in conjunction with a cooperating tool or spacer that can be gripped by the inserter/impactor.) Exemplary suitable artificial intervertebral discs include, but are not limited to, the artificial intervertebral disc 160 described herein and the artificial intervertebral discs described in the '160 application with regard to FIGS. 8a–y, 9a–t, 10a–t, 11a–j, and 12a–o thereof and by the accompanying descriptions therefor (e.g., embodiments identified as the first, second, third, fourth, and fifth preferred embodiments of the fourth embodiment family, etc.). Regarding the features suitable for being manipulated by the inserter/impactor 4000, such features include those discussed above as being suitable features on the disc 160, namely, an anteriorly facing flat surface on the second (e.g., lower) baseplate of the trial or disc, flanked by two anterolaterally facing flat surfaces (one on each side of the anteriorly facing flat surface), and, to provide for holding of the trial or disc for an anterior insertion approach, a hole spaced from the anteriorly facing flat surface, the hole having a longitudinal axis parallel to the anteriorly facing flat surface. Further regarding the features suitable for being manipulated by the inserter/impactor, such features further include the inwardly facing surfaces of the baseplates of the disc.

More particularly, the inserter/impactor 4000 includes a shaft 4020 having a distal end 4040 that has angled flat surfaces 4200a–c corresponding to and fittable against angled flat surfaces of the artificial intervertebral disc (e.g., the surfaces 180a–c of the artificial intervertebral disc 160) to be implanted. The distal end 4040 has angled flat surfaces 4200d–f corresponding to and fittable against angled flat surfaces of the artificial intervertebral disc. (e.g., the surfaces 180d–f of the artificial intervertebral disc 160) to be implanted. The distal end 4040 has a wedge-shaped extension 4042 including upper 4200g and lower 4200h wedge surfaces corresponding to and fittable against the inwardly facing surfaces of the artificial intervertebral disc (e.g., the lower surface 164a of the upper baseplate 168a of the disc 160, and the upper surface 164b of the lower baseplate 168b of the disc 160, respectively) to be implanted. For example, in an anterior approach for the disc 160 (as shown in FIGS. 4a–e), 180a and 180d facing 4200a and 4200d, 180b and 180e facing 4200b and 4200e, 180c and 180f facing 4200c and 4200f, and 164a facing 4200g and 164b facing 4200h.

The inserter/impactor 4000 holds the disc 160 in a preferred position with respect to the inserter/impactor 4000. (It should be understood that the surfaces of the wedge-shaped extension 4042 can be modified within the scope of the present invention to hold the disc 160 (or another orthopedic device) at positions other than those illustrated herein.) In the illustrated embodiment of the inserter/impactor 4000 in use with the disc 160, the preferred position is with the baseplates 168a,b of the disc 160 angle at 15 degrees of lordosis with respect to one another. More particularly, preferably, the upper and lower surfaces (e.g., 4200g and 4200h) of the wedge-shaped extension 4042 protrude from the distal end 4040 and are formed to hold the baseplates 168a,b such that they are angled at 15 degrees of lordosis with respect to one another. A surface (e.g., lower surface 4200h) of the wedge-shape extension 4042 that mates with an inwardly facing surface of a baseplate (e.g., the lower baseplate 168b) of a disc (e.g., 160) may be correspondingly shaped (e.g., curved or flat) for interaction or mating with the disc baseplate (e.g., the lower surface 4200h of the wedge-shaped extension as illustrated is curved to accommodate the surface of the shield of the disc). Preferably, the forward surface 4200i of the wedge-shaped extension 4042 has a concave curvature towards the shaft 4020 of the inserter/impactor 4000, also for accommodating the curvature of the surface of the shield of the disc.

Also preferably with regard to the preferred positioning, the wedge surfaces of the distal end 4040 protrude from a distance midway with respect to the top and bottom of the distal end 4040 and span (e.g., right to left or vice-versa) the entire distal face of the distal end 4040, and the surfaces 4200d–f above the wedge on the distal end 4040 are respectively perpendicular to the wedge's upper surface 4200g such that each is disposed in parallel with its respective corresponding surface of the disc 160 when the disc 160 is held by the inserter/impactor 4000 at the appropriate lordosis angle. (And, accordingly, are angled approximately 15 degrees with respect to the surfaces below the wedge 4200a–c.) Preferably, for an anterior approach, the wedge-shaped extension 4042 is designed and shaped to fit with its antero-lateral confronting surfaces (4200d,f and 4200a,c) tightly against the correspondingly antero-laterally facing surfaces (180d,f and 180a,c) of the disc 160, but such that its anterior confronting surfaces (4200e and 4200b) are slightly spaced from the anteriorly facing surfaces (180d and 180b) of the disc 160, when the disc is held by the inserter/impactor 4000. This is primarily to address manufacturing issues (in some cases, tolerances may not be adequately defined to ensure that all of those surfaces fit tightly against their corresponding surfaces), so that if there are manufacturing anomalies, any slight tolerance differences that may exist are nevertheless still adequate to ensure at least the tight fitting of the antero-lateral confronting surfaces, so that manipulation of the disc 160 is possible (e.g., in the manner of a wrench against an angled nut). This can be achieved, e.g., by designing the anterior confronting surfaces (4200e and 4200b) to each be slightly greater in length than the corresponding anteriorly facing surfaces (180e and 180b) of the disc baseplates, while still being angled with respect to the antero-lateral confronting surfaces (4200d,f and 4200a,c) at the same angle the antero-laterally facing surfaces (180d,f and 180a,c) of the disc baseplates are angled with respect to the anteriorly facing surfaces (180e and 180b) of the disc. The increased length of the anterior confronting surfaces on the wedge extension results in the slight clearance between the anteriorly facing surfaces (180e and 180b) of the disc and the corresponding anterior confronting surface (4200e and 4200b) of the wedged distal end, thereby ensuring that the disc will be fully seated against the antero-lateral confronting surfaces of the distal end despite possible manufacturing, material or other inevitable variations in tolerances of the artificial intervertebral disc or the inserter/impactor. As noted above, similar in this regard to the manner in which a wrench engages a nut, this fitting increases the mechanical advantage toward repositioning the disc in the intervertebral space. It should be noted, inasmuch as the inserter/impactor 4000 described herein can engage the disc from the antero-lateral angles as well, the anterior confronting surfaces (4200e and 4200b) should also be longer than the antero-laterally facing surfaces (180d,f and 180a,c) of the disc, so that a similar fitting occurs when the disc is held from the antero-lateral angles. Stated broadly, the primary confronting surfaces (e.g., the anterior confronting surfaces) of the inserter/impactor are preferably slightly longer than the primary confronted surfaces (e.g., anteriorly facing surfaces) of the disc for any given holding orientation.

Further, the inserter/impactor 4000 includes a holding pin 4080 that extends from the wedge 4042 along a longitudinal axis of the shaft 4020, the pin 4080 having a distal end 4100 that is bent downwardly. The holding pin 4080 is spring loaded (e.g., by a spring 4090) in a central channel of the shaft 4020, so that it is biased toward the shaft 4020 (preferably, the bent end 4100 of the pin 4080 prevents it from entering the central channel). The holding pin 4080 is restricted from upwardly lateral movement with respect to the distal end of the inserter/impactor by the presence of the wedge-shaped extension 4042 of the distal end 4040 of the inserter/impactor 4000. More particularly, with any attempted upward movement of the holding pin 4080, the pin encounters the upper surface of the channel in which the pin 4080 travels, preventing any such upward movement. The holding pin 4080 is preferably heat treated (e.g., cold formed) to increase material quality (e.q., strength).

A flange 4110, mechanically connected to the pin 4080 and translating adjacent the shaft 4020, can be pushed distally to overcome the bias of the spring 4090 to space the pin 4080 away from the wedge 4042. (An alternative configuration is one in which the flange 4110 and the pin 4080 are formed from a single piece, rather than being mechanically connected.) In this extended position, the pin 4080 can be inserted in a hole (e.g., 182b) in the baseplate (e.g., 168b) of the artificial intervertebral disc (e.g., 160). Releasing the flange 4110 allows the spring 4090 to pull the pin 4080 back, causing the anteriorly facing surface 180b of the baseplate 168b to be held against the lower central flat surface 4200b of the inserter/impactor 4000. This can be further understood in light of the description of the manner in which the inserter/impactor of the '160 application functions to grip an orthopedic device, which is included in the '160 application and incorporated by reference herein. Simultaneously, the anteriorly facing surface 180e of the baseplate 168a is pulled against the upper central flat surface 4200e of the inserter/impactor 4000 and the anteriolaterally facing flat surfaces 180d,f of the artificial intervertebral disc 160 is pulled against the other corresponding flat surfaces 4200d,f of the inserter/impactor 4000. Additionally, the upper and lower wedge surfaces (4200g,h) interfere between the inwardly facing surfaces 164a,b of the disc baseplates, causing the baseplate to be angled at a 15 degree lordosis angle, with the lower surface 164a of the upper baseplate 168a held against the upper surface 4200g, and the upper surface of the shield being held against the lower surface 4200h, as best shown in FIGS. 4a–e.

A knob 4120, threaded on the shaft 4020, can be rotated about the longitudinal axis of the shaft 4020 to push the flange 4110 farther proximally, to pull the pin 4080 tighter and therefore lock its position (the interference of the threads of the knob-shaft interface prevents the knob 4120 from moving distally unless the knob 4120 is reverse rotated to effect that result) to more securely hold the baseplate 168b, and reverse rotated to unlock and loosen the pin 4080.

When the disc 160 is held in this manner, rotation of the disc 160 about a longitudinal axis (of the disc 160) relative to the inserter/impactor 4000 is prevented by interference of the corners of the disc's 160 flat surfaces (180a–c and 180d–f) and the corners of the inserter/impactor's 4000 flat surfaces (4200a–c and 4200d–f), similar to the manner in which a wrench holding a nut prevents rotation of the nut relative to the wrench. Further, the holding of the disc 160 in this manner allows for some repositioning of the disc 160 in the intervertebral space via rotation of the disc 160 in either direction about the longitudinal axis of the intervertebral space. Further when the disc is held in this manner, rotation of the disc about a lateral axis (of the disc 160) relative to the inserter/impactor 4000 is prevented by interference of the inwardly facing surface 164a of the first baseplate (e.g., upper baseplate) of the disc and the upper surface 4200g of the wedge on the distal end 4040, and by interference of the inwardly facing surface 164b of the second baseplate (e.g., lower baseplate) of the disc and the lower surface 4200h of the wedge on the distal end 4040. Accordingly, the holding of the disc in this manner allows for some repositioning of the disc in the intervertebral space via rotation of the disc in either direction about the longitudinal or latitudinal axis of the intervertebral space.

In some embodiments, when the artificial intervertebral disc 160 is held by the inserter/impactor 4000, the flat surfaces 180a–c are more closely confronted by the angled flat surfaces 4200a–c of the inserter/impactor 4000, compared with the flat surfaces 180d–f being less closely confronted by the angled flat surfaces 4200d–f of the inserter/impactor 4000. As such, the structure of the artificial intervertebral disc 160 having the flat surfaces 180d–f (e.g., the upper baseplate 168a) has slightly more rotation and angulation freedom relative to the inserter/impactor 4000 when being held, compared to the structure of the artificial intervertebral disc 160 having the flat surfaces 180a–c (e.g., the lower baseplate 168b). This permits the artificial intervertebral disc 160 to adjust to the intervertebral space (e.g., to the angulation of the adjacent vertebral endplates, defining the intervertebral space, relative to one another) as it is being inserted thereinto. That is, typically, the adjacent vertebral endplates will be lordotically angled with respect to one another as a result of the intervertebral space being prepared and distracted.

Preferably, in order to provide for a holding of the disc 160 for two additional (here, anteriolateral) insertion approaches, each disc 160 also includes two additional holes 182a and 182c, one (e.g., 182a) spaced apart from one of the anteriolaterally facing flat surfaces (e.g. 180a), and the other (e.g. 182c) spaced apart from the other of the anteriolaterally facing flat surfaces (e.g. 180c). Accordingly, operation of the inserter/impactor 4000 can fit the holding pin 4080 into either of these two additional holes 182a or 182c, and hold the associated anteriolaterally facing flat surface (the one associated with the hole into which the pin 4080 is fit) of the disc 160 against the flat surface of the inserter/impactor 4000 opposite the pin 4080. For example, in a first anteriolateral approach for the disc 160, 180a and 180d facing 4200b and 4200e, 180c and 180f not confronted, and 180b and 180e facing 4200c and 4200f, and in a second anteriolateral approach for the disc 160, 180b and 180e facing 4200a and 4200d, 180a and 180d not confronted, and 180c and 180f facing 4200b and 4200e. It should be understood that preferably, in order to facilitate these additional approaches, the angle separating the anteriorly facing flat surface of the disc 160 and one of the anteriolaterally facing flat surfaces of the disc 160 is equal to the angle separating the anteriorly facing flat surface and the other of the anteriolaterally facing flat surfaces. Preferably, the surfaces are angled with respect to one another at an angle of 33.4 degrees.

It should also be understood that the inclusion of additional adjacent angulated surfaces (or placing the angulated surfaces in other locations on the disc or other orthopedic device), and/or including corresponding holes adjacent to such surfaces, can provide the surgeon with additional approaches, e.g., other anteriolateral approaches, directly lateral approaches, posteriolateral approaches, and/or directly posterior approaches. For example, a trial or disc can have angled surfaces (and corresponding holes) along the entire perimeter of one or both of the baseplates, and thus enable the surgeon to engage the trial or disc from a number of angles, including anterior, posterior, lateral, anteriolateral, and posteriolateral angles.

The inserter/impactor 4000 further includes at a proximal end a cap 4140 for use as an impact surface if the disc 160 must be impacted further into the intervertebral space after insertion, or forcibly extracted from the intervertebral space. A mallet can be used to strike the cap 4140 (in a distal direction for impaction, or in a proximal direction (using the flange of the cap 4140) for extraction). It should be noted a striking of the cap 4140 will translate the striking force to the baseplates through the shaft 4020 and the flat surfaces, but will not damage the holding pin 4080 because the holding pin 4080 is spring loaded in the central channel and thus buffered from the striking force thereby. The distal end 4040 of the inserter/impactor 4000 further preferably includes at least one vertebral body stop 4202 that protrudes longitudinally with respect to the shaft 4020, from the surfaces of the distal end. The stops help prevent the inserter/impactor from being used to insert the disc (or other orthopedic device) too far into the intervertebral space.

Accordingly, the inserter/impactor 4000 can be used to grip the artificial intervertebral disc to be implanted, and hold the same during insertion and/or removal of the same, and is useful for a variety of surgical approach angles.

While there has been described and illustrated specific embodiments of instrumentation, it will be apparent to those skilled in the art that variations and modifications are possible without deviating from the broad spirit and principle of the invention. The invention, therefore, shall not be limited to the specific embodiments discussed herein.

What is claimed is:

1. A holding instrument for an implant comprising:
a shaft having a proximal end, a distal end and a longitudinal axis extending between said proximal and distal ends; a body attached to said distal end of said shaft having at least one concave surface comprising a first set of substantially flat surfaces that are angled relative to one another, wherein said body further comprises a second set of substantially flat surfaces that are angled relative to one another, said second set of substantially flat surfaces being spaced from said first set of substantially flat surfaces, and a projection having a concave surface provided between said first set of substantially flat surfaces and said second set of substantially flat surfaces;

a pin extendable from said body attached to said distal end of said shaft, said pin having a hooked end, said pin being movable between a retracted position and an extended position;

a spring coupled with said pin for normally urging said pin into the retracted position;

a flange coupled with said pin, said flange being movable relative to said shaft and toward said distal end of said shaft for extending said hooked end of said pin from said body attached to said distal end of said shaft.

2. The instrument as claimed in claim 1, wherein said pin has a first section that extends along said longitudinal axis of said shaft and said hooked end is connected to said first section of said pin.

3. The instrument as claimed in claim 1, wherein said hooked end of said pin comprises a single hook.

4. The instrument as claimed in claim 1, wherein said projection further comprises a substantially flat upper surface extending from said concave surface of said projection toward said proximal end of said instrument and a substantially flat lower surface extending from said concave surface of said projection toward said proximal end of said instrument.

5. The instrument as claimed in claim 4, wherein said substantially flat upper surface of said projection and said substantially flat lower surface of said projection are angled relative to one another.

6. The instrument as claimed in claim 1, wherein said projection includes a channel having an opening and said hooked end of said pin is extendable from said channel.

7. The instrument as claimed in claim 1, further comprising a knob coupled to said shaft, wherein said knob is rotatable in a first direction for locking said flange from movement relative to said shaft and is rotatable in a second direction for unlocking said flange to allow for movement of said flange relative to said shaft.

8. The instrument as claimed in claim 1, further comprising a vertebral body stop extending upwardly from said body attached to said distal end of said shaft.

* * * * *

UNITED STATES PATENT AND TRADEMARK OFFICE
CERTIFICATE OF CORRECTION

PATENT NO.        : 7,235,081 B2                                            Page 1 of 1
APPLICATION NO.   : 10/425267
DATED             : June 26, 2007
INVENTOR(S)       : Joseph P. Errico, Michael W. Dudasik and Rafail Zubok It is certified that error appears in the above-identified patent and that said Letters Patent is hereby corrected as shown below:

Column 3, line 14, delete the phrase "FIG. 1" and insert the phrase --FIGS. 1A-H--.
Column 3, line 15, delete the phrase "FIG. 1" and insert the phrase --FIGS. 1A-H--.
Column 3, line 45, delete the phrase "FIG. 1" and insert the phrase --FIGS. 1A-H--.
Column 4, line 59, delete the phrase "FIG. 1" and insert the phrase --FIGS. 1A-H--.
Column 7, line 35, delete the word "FIG." and insert the words --FIGS.--
Column 7, line 37, delete "11-h" and insert --11a-h--.

Signed and Sealed this

Seventeenth Day of June, 2008

JON W. DUDAS
*Director of the United States Patent and Trademark Office*